US00PP15454P2

(12) United States Plant Patent
Bunnik

(10) Patent No.: US PP15,454 P2
(45) Date of Patent: Dec. 21, 2004

(54) ***CYPERUS* PLANT NAMED 'PERKAMENTUS COMPACT'**

(50) Latin Name: *Cyperus papyrus*
Varietal Denomination: Perkamentus Compact

(75) Inventor: Johannes Jacobus Petrus Maria Bunnik, Bleiswijk (NL)

(73) Assignee: Bunnik Plants BV, Bleiswijk (NL)

( * ) Notice: Subject to any disclaimer, the term of this patent is extended or adjusted under 35 U.S.C. 154(b) by 0 days.

(21) Appl. No.: 10/766,781

(22) Filed: Jan. 28, 2004

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Cyperus* plant named 'Perkamentus Compact', characterized by its compact plant habit; upright growth habit; relatively short stems; and elongated slender green-colored rays subtending the inflorescences.

1 Drawing Sheet

Botanical classification/cultivar designation: *Cyperus papyrus* cultivar Perkamentus Compact.

BACKGROUND OF THE INVENTION

The present Invention relates to a new and distinct cultivar of Perkamentus plant, botanically known as *Perkamentus papyrus,* and hereinafter referred to by the cultivar name Perkamentus Compact.

The new *Cyperus* is a naturally-occurring whole plant mutation of *Cyperus papyrus* cultivar Perkamentus, not patented. The new *Cyperus* was discovered and selected by the Inventor as a plant within a population of plants of the parent selection in a controlled environment in Bleiswijk, The Netherlands.

Asexual reproduction of the new cultivar by tissue culture micropropagation at Bleiswijk, The Netherlands since June, 2002, has shown that the unique features of this new *Cyperus* are stable and reproduced true to type in successive generations.

SUMMARY OF THE INVENTION

The following traits have been repeatedly observed and are determined to be the unique characteristics of 'Perkamentus Compact'. These characteristics in combination distinguish 'Perkamentus Compact' as a new and distinct *Cyperus* cultivar:

1. Compact plant habit.
2. Upright growth habit.
3. Relatively short stems.
4. Elongated slender green-colored rays subtending the inflorescences.

Plants of the new *Cyperus* are most similar to plants of the parent cultivar Perkamentus. In side-by-side comparisons conducted in Bleiswijk, The Netherlands, plants of the new *Cyperus* differed from plants of the cultivar Perkamentus primarily in plant height as plants of the new *Cyperus* were about 25% shorter than plants of the cultivar Perkamentus.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which more accurately describe the actual colors of the new *Cyperus*.

The photograph comprises a side perspective view of a typical plant of 'Perkamentus Compact' grown in a container.

DETAILED BOTANICAL DESCRIPTION

The cultivar Perkamentus Compact has not been observed under all possible environmental conditions. The phenotype may vary somewhat with variations in environment such as temperature and light intensity, without, however, any variance in genotype. The aforementioned photograph and the following observations and measurements describe plants grown in Bleiswijk, The Netherlands under commercial practice in a glass-covered greenhouse with day and night temperatures about 20° C. Plants used in the photograph and following description were about two years old and grown in 12-cm containers. In the following description, color references are made to The Royal Horticultural Society Colour Chart, 2001 Edition, except where general terms of ordinary dictionary significance are used.

Botanical classification: *Cyperus papyrus* cultivar Perkamentus Compact.

Parentage: Naturally-occurring whole plant mutation of *Cyperus papyrus* cultivar Perkamentus, not patented.

Propagation:

*Type.*—By tissue culture.

*Time to initiate roots on a micropropagated plantlet.*—About six weeks at 20° C.

*Time to produce a rooted micropropagated plant.*—About twelve weeks at 20° C.

*Root description.*—Fibrous; rhizome development has not been observed.

Plant description:

*General appearance.*—Upright growth habit; compact plant habit; numerous relatively short erect stems. Overall plant shape is an inverted triangle. Numerous elongated slender green-colored rays at base of flower spikes. Moderately vigorous.

*Plant height.*—About 30 cm.

*Plant diameter.*—About 30 cm.

*Stem description.*—Quantity per plant: About ten main stems and about 36 lateral stems at main stem apices. Length: Main stems, about 19.9 cm; lateral stems, about 2.3 cm. Diameter: Main stems, about 1.2 cm; lateral stems, about 2 mm. Internode length: About 1.6 cm. Strength: Strong. Cross-section: Triangular. Texture: Smooth, glabrous. Color: Main stems, 137A, towards the base, 144A to 144B; lateral stems, 191B, towards the base, 199D.

*Foliage description.*—Leaves reduced to sheaths at base of stems, brownish in color; roughly deltoid in shape.

Flower description:

*Flower type and flowering habit.*—Minute single sessile flowers arranged in terminal compound spikes with numerous spikelets; about 24 flowers per spike. Flowers not persistent. Flowers not fragrant. Flowers face upright to slightly outwardly.

*Flowering season.*—Plants typically flower during the autumn in The Netherlands; flowering continuously during this period.

*Inflorescence length.*—About 1.1 cm.

*Inflorescence diameter.*—About 7 mm.

*Flower diameter.*—About 2 mm.

*Flower depth.*—About 4 mm.

*Flower buds.*—Length: About 2.5 mm. Diameter: About 0.5 mm. Shape: Narrowly lanceolate. Color: 146C to 146D.

*Involucral bracts.*—Quantity: Two per spike. Length: About 4 cm. Width: About 0.5 mm. Shape: Linear to lanceolate. Apex: Acute. Color: 139B.

*Rays.*—Arrangement: In terminal rosettes. Length: About 9.4 to 11.8 cm. Width: About 3 mm to 1.1 cm. Shape: Filiform; elongated, slender. Apex: Elongated acute. Base: Cuneate. Margin: Entire. Texture, upper and lower surfaces: Smooth, glabrous. Venation pattern: Parallel. Color: Developing rays, upper surface: 141A. Developing rays, lower surface: Between 137A and 141A. Fully expanded rays, upper surface: Between 137A and 141A. Fully expanded rays, lower surface: 198D; central band, 137A. Venation, upper surface: Between 137A and 141A. Venation, lower surface: 137A.

*Scales.*—Quantity/arrangement: About three per flower; imbricate. Length: About 1.5 mm. Width: About 0.5 mm. Shape: Narrowly lanceolate. Apex: Acute. Base: Cuneate. Margin: Entire. Texture, upper and lower surfaces: Smooth, glabrous. Color: When developing and fully developed, upper surface: 148B to 157C. When developing and fully developed, lower surface: 148B to 157C.

*Peduncles.*—Length: About 5.5 cm. Diameter: About 1 mm. Angle: About 0 to 30° from vertical. Strength: Strong. Texture: Smooth, glabrous. Color: Between 137A to 141A.

*Reproductive organs.*—Androecium: Quantity per flower: About three. Stamen length: About 1 mm. Stamen width: About 0.1 mm. Anther shape: Narrowly elliptic to linear. Anther color: Close to 172B. Amount of pollen: None observed. Gynoecium: Quantity per flower: One. Pistil length: About 2 mm. Stigma shape: Three-parted. Stigma color: N170A to N170B. Style length: About 1.8 mm. Style color: N170A to N170B. Ovary color: 147C to 147D.

*Seed/fruit.*—Seed and fruit development has not been observed.

Disease/pest resistance: Plants of the new *Cyperus* have not been observed to be resistant to pathogens and pests common to *Cyperus*.

Temperature tolerance: Plants of the new *Cyperus* have been observed to tolerate temperatures from about 5 to 35° C.

It is claimed:

1. A new and distinct cultivar of *Cyperus* plant named 'Perkamentus Compact', as illustrated and described.

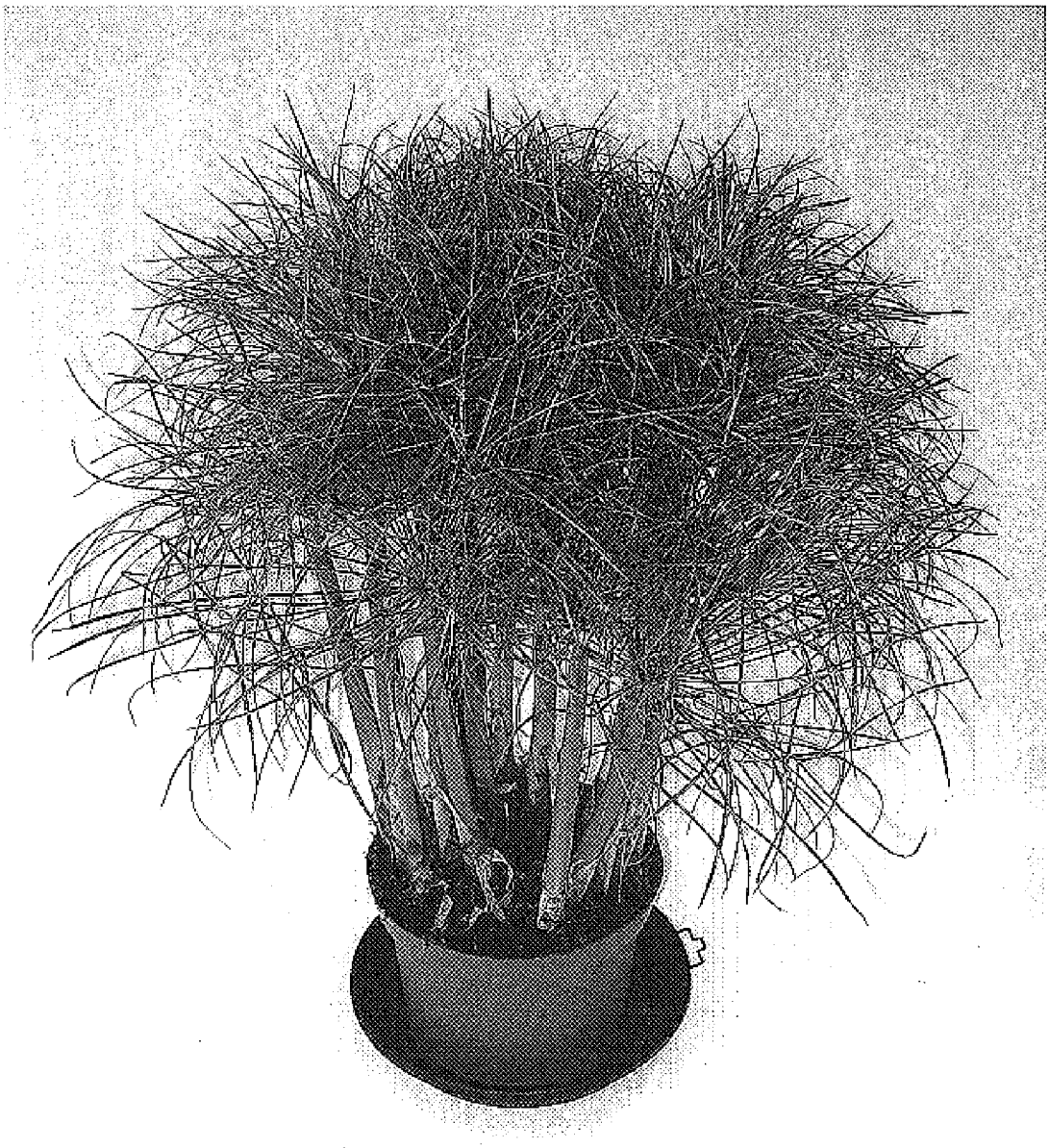

* * * * *